United States Patent
Rife et al.

(10) Patent No.: US 9,366,013 B2
(45) Date of Patent: Jun. 14, 2016

(54) WATER DISPENSER DECONTAMINATION DEVICE

(71) Applicants: Robert Rife, Mt. Pleasant, SC (US); Genevieve Stratos, Sullivan's Island, SC (US)

(72) Inventors: Robert Rife, Mt. Pleasant, SC (US); Genevieve Stratos, Sullivan's Island, SC (US)

(*) Notice: Subject to any disclaimer, the term of this patent is extended or adjusted under 35 U.S.C. 154(b) by 0 days.

(21) Appl. No.: 14/706,030

(22) Filed: May 7, 2015

(65) Prior Publication Data
US 2015/0330064 A1 Nov. 19, 2015

Related U.S. Application Data

(60) Provisional application No. 61/993,768, filed on May 15, 2014.

(51) Int. Cl.
| | | |
|---|---|---|
| E03B 9/20 | (2006.01) |
| A61L 2/10 | (2006.01) |
| B05B 15/02 | (2006.01) |
| C02F 1/32 | (2006.01) |

(52) U.S. Cl.
CPC ...... *E03B 9/20* (2013.01); *A61L 2/10* (2013.01); *B05B 15/02* (2013.01); *C02F 1/325* (2013.01); *C02F 2201/3227* (2013.01); *C02F 2307/10* (2013.01)

(58) Field of Classification Search
CPC .............. E03B 9/18; E03B 9/20; A61L 2/10; B05B 15/02; B05B 15/10; B05B 17/08
See application file for complete search history.

(56) References Cited

U.S. PATENT DOCUMENTS

| | | | |
|---|---|---|---|
| 2,756,470 A | 7/1956 | Sawchuck | |
| 4,081,134 A | 3/1978 | Anderson | |
| 4,899,057 A | 2/1990 | Koji | |
| 2002/0139865 A1* | 10/2002 | Mulvaney | A61L 2/08 239/20 |
| 2007/0125230 A1* | 6/2007 | Powell | B05B 17/08 95/210 |
| 2010/0327073 A1* | 12/2010 | Kette | B05B 17/08 239/8 |
| 2012/0037487 A1* | 2/2012 | Wang | C02F 1/18 202/185.3 |
| 2013/0332239 A1* | 12/2013 | Matre | G06Q 30/0206 705/7.35 |

FOREIGN PATENT DOCUMENTS

| | | |
|---|---|---|
| KR | 1020090081554 | 7/2009 |
| KR | 200452878 | 3/2011 |

OTHER PUBLICATIONS

PCT International Search Report and Written Opinion, mailing date Nov. 27, 2015.

* cited by examiner

*Primary Examiner* — Ryan Reis
(74) *Attorney, Agent, or Firm* — B. Craig Killough; Barnwell Whaley Patterson & Helms

(57) ABSTRACT

A water dispenser includes a decontamination device. The dispenser has a plurality of channels that communicate with a water supply. The channels are intermittently exposed to pathogen killing radiation during operation of the water dispenser.

19 Claims, 4 Drawing Sheets

WATER DISPENSER DECONTAMINATION DEVICE

FIELD OF THE INVENTION

This invention relates to dispensing of potable water in public facilities and is more particularly directed to decontamination of water dispensing devices such as drinking fountains.

BACKGROUND OF THE INVENTION

Water dispensing devices, such as drinking fountains, are highly bacteria laden public utilities. Studies have shown that public drinking fountains often have higher bacteria counts than public toilet seats and floors in public buildings.

There is a need to reduce bacterial counts at water fountains so that individuals do not ingest potentially harmful bacteria. The decontamination process should be designed to continuously, even if periodically, kill pathogens while the water dispensing device is in service.

C-band ultraviolet radiation (UV-C) is effective in significantly reducing bacterial loads that are present on objects exposed to UV-C. Extended UV-C exposure is harmful to humans.

SUMMARY OF THE INVENTION

The present invention is a water dispenser or drinking fountain that includes a decontamination device. The invention has a plurality of channels that are used in a sequence, and which communicate with a water supply. The channels are exposed to decontaminating radiation while the water dispenser is in service. Parts of the water dispenser or drinking fountain may be formed of bacteria resistant materials.

DRAWING DESCRIPTION

DESCRIPTION OF PREFERRED EMBODIMENTS

Figure 1:
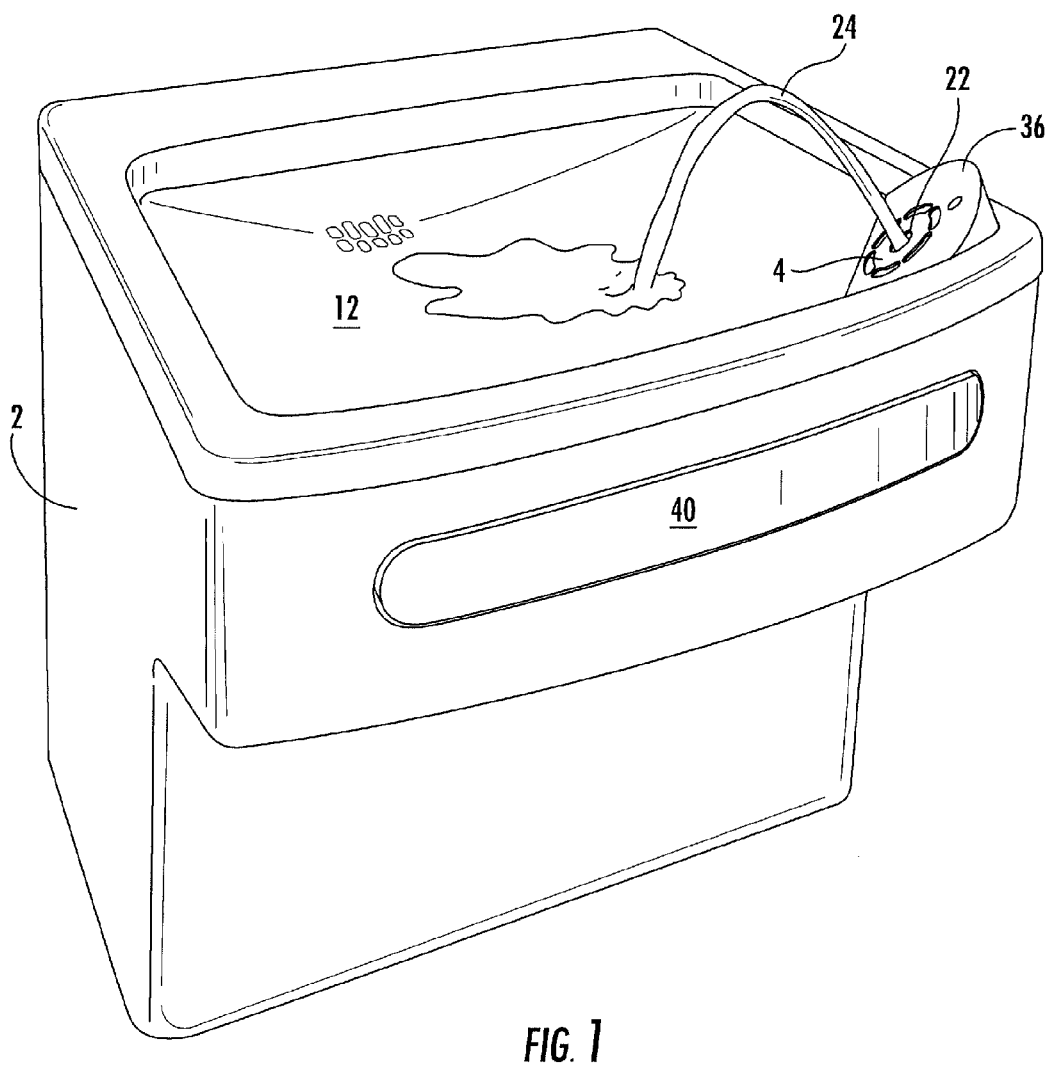
FIG. 1 is a perspective view of a water dispenser or drinking fountain incorporating the invention.

Turning now to the drawing figures, FIG. 1 shows a water dispenser or drinking fountain 2 according to a preferred embodiment of the invention. The water spout 36 portion of the drinking fountain may a flat surface that surrounds the opening 22 for the water outlet, but the portion of the spout having in which the opening is present is preferred to have a concave, or dish shape, or a similarly inwardly disposed surface 4 that discourages a user, such as a child, from placing his or her mouth on the water spout.

The water runoff surface 12 is preferred to be constructed of a material having antimicrobial properties. Copper and silver ions are examples of materials having antimicrobial properties. It is preferred for the water runoff to be constructed of materials that comprise metal ions having antimicrobial properties. Alternatively, antimicrobial ceramics may be used.

Figure 2:
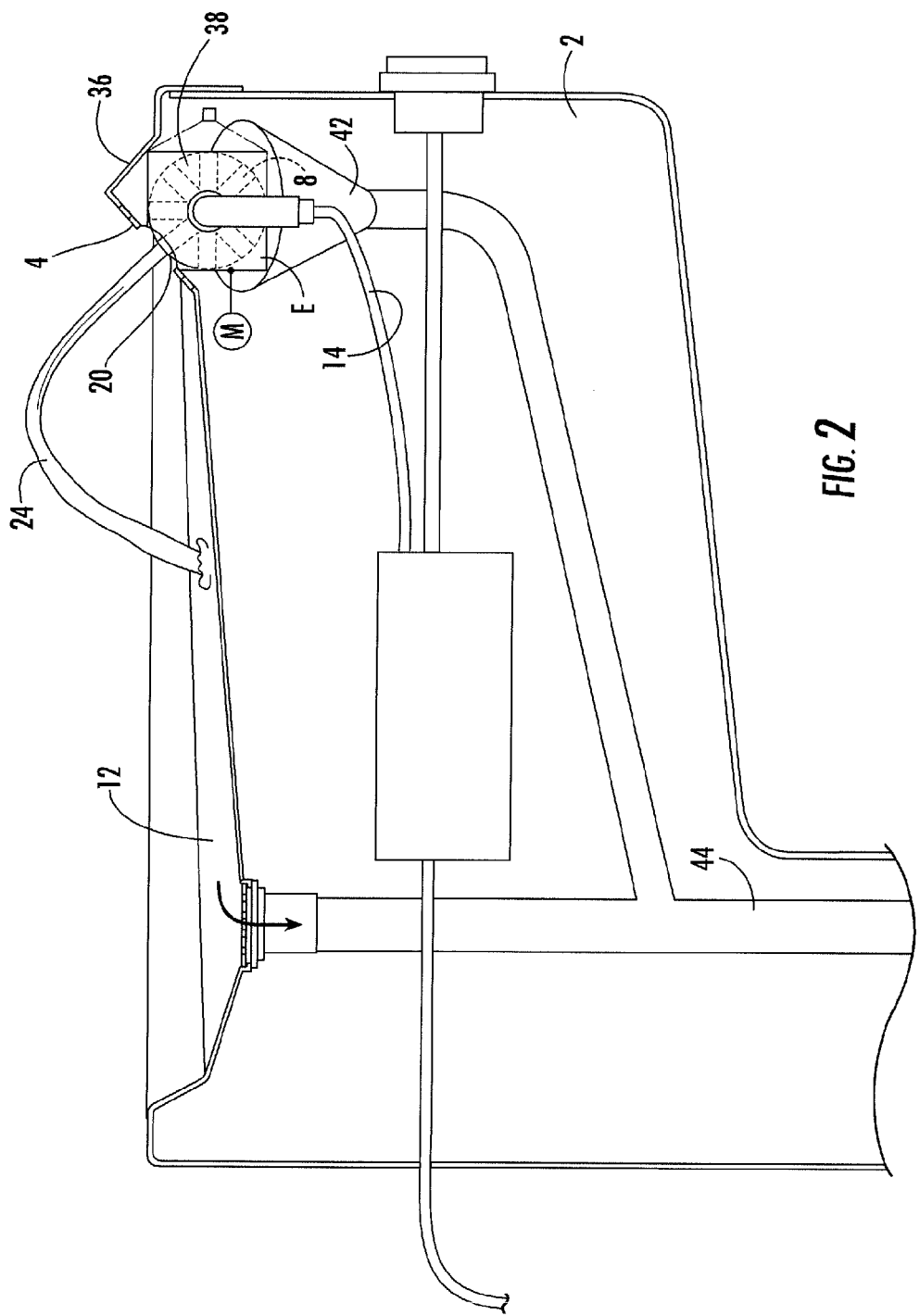
FIG. 2 is a side sectioned view of a water dispenser or drinking fountain.

In a preferred embodiment of the invention, a decontamination unit 6 is positioned within a body of the drinking fountain, and may be positioned adjacent to the spout of the drinking fountain and within the body of the water dispensing device 2. FIG. 2. The body of the water dispensing device is preferred to be opaque to radiation emitted by the radiation emitter or emitters 16, and acts as a shield or guard, thereby preventing a user of the water dispensing device from being exposed to radiation.

In the embodiment shown in the drawing figures, the decontamination unit has a plurality of water emitting channels 8. The decontamination unit is preferred to have at least 3 channels, and may have more. In one embodiment, as many as 8 channels may be used with a drinking fountain of the type and size that is in common use in public facilities.

The plurality of channels may be formed in a rotating member, or wheel 38, with each of the channels joining at the center of the wheel. A water inlet 14 provides water under pressure from a water supply to the center of the wheel, with water distributed to each of the channels by communication from the center of the wheel.

Figure 3:
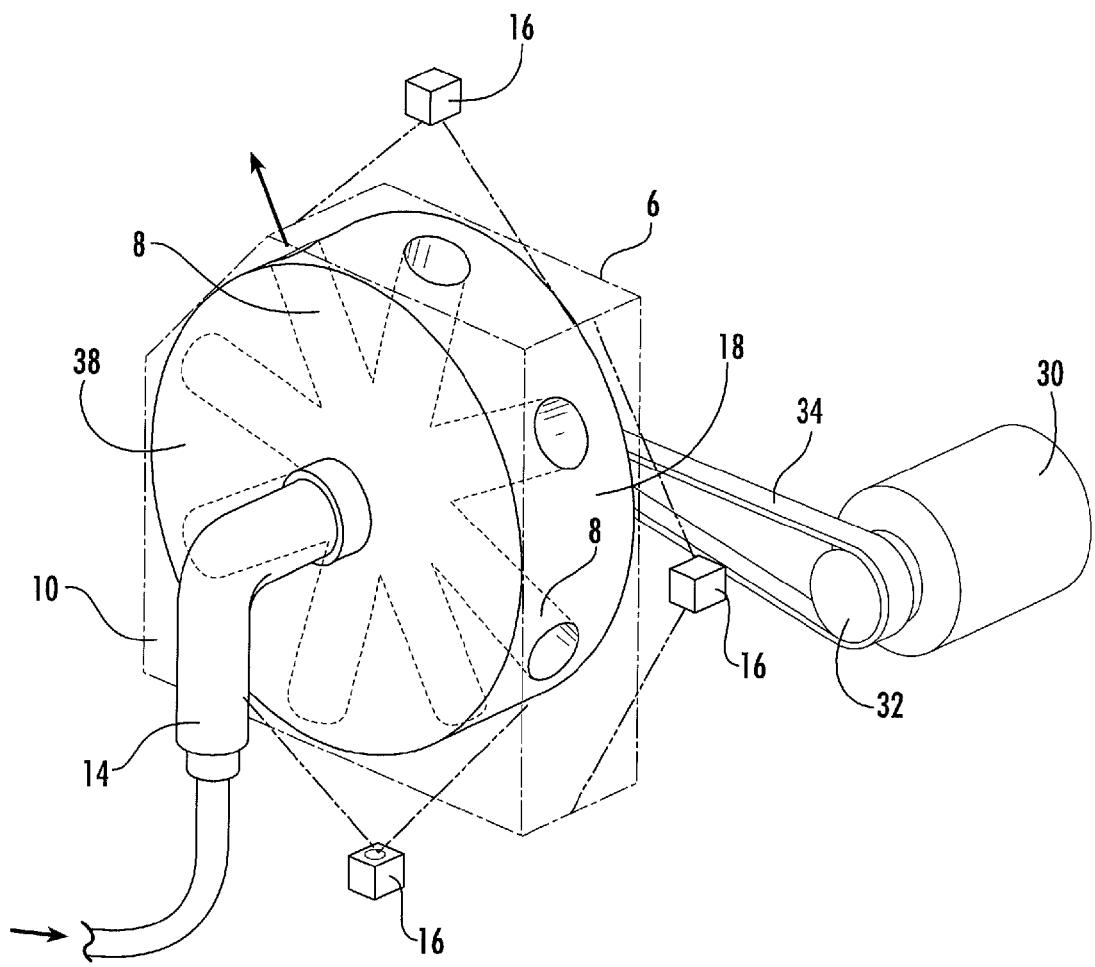
FIG. 3 is an isolation of an embodiment of the decontamination device according to the invention.
Figure 4:
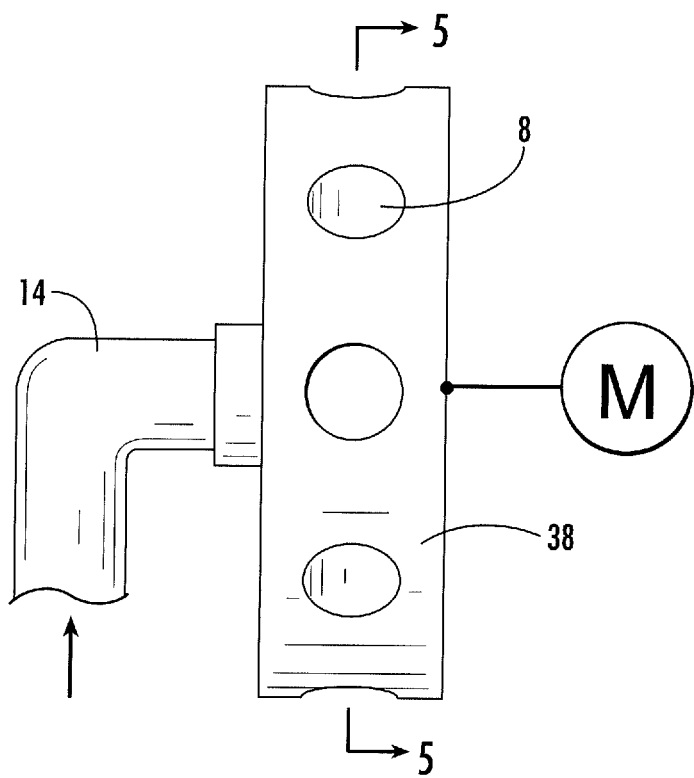
FIG. 4 shows a wheel of a decontamination device according to an embodiment of the invention.
Figure 5:
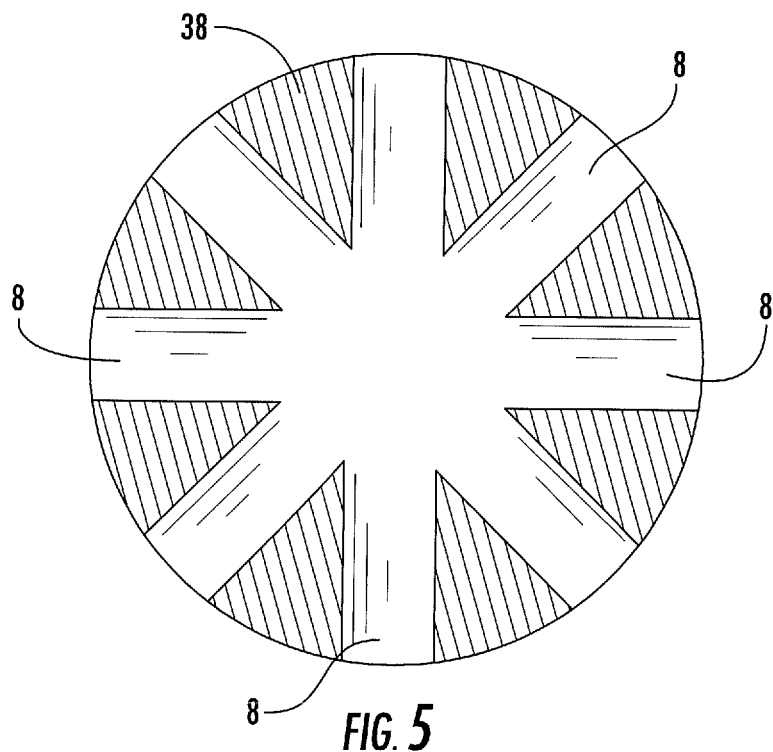
FIG. 5 is a sectioned view taken essentially along line 5-5 of FIG. 4.

The rotating wheel may be contained in a radiation transparent outer housing 10 that may be part of the decontamination unit. A plurality of radiation emitters 16 may be positioned around the housing according to a preferred embodiment, and as shown in FIG. 3. The emitters may emit antimicrobial radiation such as UV-C radiation.

In the embodiment shown, the wheel is contained in a generally circular housing 18 that abuts an outlet of each of the channels and prevents water from escaping from the outlets of the channels that are not active. The outer housing and the generally circular housing each have an opening 20 therein that aligns and communicates with an opening 22 in the body of the drinking fountain. The openings 20,22 and one of the channels permit water to flow from the water dispenser, such as a drinking fountain. When one of the channels of the rotating wheel aligns with the openings 20,22, water flows through the inlet and into the wheel, and out of the channel that is aligned with the opening in the housing. The generally circular housing acts as a closed valve to prevent water from escaping channels that are not aligned with opening 20, and as an open valve (by means of the opening in it) to permit water to flow from the channel that is aligned with the opening. The channel that is aligned with the opening to dispense water is designated as the active channel. Water 24 is emitted through the active channel and from the spout as shown in FIG. 2.

Other devices, such as valves within each of the channels that are electrically, hydraulically or pneumatically actuated may be used to cause one channel to be the active channel, while the remaining channels are inactive.

In the embodiment of FIG. 2, the active channel of the wheel 38 protrudes through an opening of the recessed surface 4. An outer surface of spout 36 surrounds surface 4. Surface 4 is preferred to be recessed from the surrounding surface of the spout. Surface 4 may by recessed by providing a concave shape for surface 4. The recessed surface in a preferred embodiment allows the upper or forward most part of the wheel to be below the adjoining structure of the spout 36, which discourages users from placing their mouth on the wheel or channel. The surface 4 is preferred to be formed of antimicrobial materials. In the embodiment as shown, a portion of the active channel of the wheel extends through surface 4, but the wheel is recessed below the portion of the spout that surrounds surface 4. Surface 4 has opening 22 therein that allows the wheel to protrude through in the embodiment of FIG. 2.

In use, when a user demands water, the user presses a switch, and a valve is actuated to allow water to flow into inlet 14 and wheel 38. In an embodiment, pressing the switch also causes the wheel to rotate so that one of the channels, which is the active channel, aligns with the openings in the housings, allowing water to flow through the active channel, and out of the water outlet spout. Rotation of the wheel may be actuated by motorized means, such as a motor 30 having a pulley 32 and a belt 34, with the belt connected to a pulley that actuates rotation of the wheel 38. Other power transmission devices may be used.

In an embodiment, a switch 40 on the water fountain actuates water flow and rotation of the wheel. The switch may be depressed to manually actuate the water fountain, or the switch may communicate with an electric eye that senses the presence of a user in front of the water fountain to actuate the water fountain.

In an embodiment, upon actuation of the water fountain, radiation is emitted from the radiation emitters. The wheel rotates into position with the spout to allow water to be dispensed from the active channel to the exterior of the water fountain. The active channel that aligns with the openings in the housings to form the spout rotates past one or all of the UV-C emitters, so as to expose the selected channel to sufficient UV-C admission to decontaminate the channel and kill harmful bacteria prior to transporting water to the user. The embodiment shown also decontaminates the remaining, inactive, channels by exposure to C Band ultraviolet (UV-C) radiation.

An electronic timer may be used to stop the water flow after a preset time. Additionally, or alternative, water flow may be terminated after the user releases the manual switch or after the electric eye no longer senses the presence of a user. As a safety feature, an electric eye or radio wave device may be positioned at or near the spout, and if a user gets too close to the spout, water flow is terminated.

Indexing of the wheel 38 may be based on elapsed time since prior use of the device. If the water dispenser or fountain has been used recently, or upon termination of water flow, the wheel may index to another channel, such as the adjacent and next channel. If the water dispenser has not been used recently, then the wheel may rotate 180-360° to increase exposure of the active channel to UV-C decontamination. For example, if the water dispenser has been activated within the past hour, the wheel indexes to the next channel become the active channel. If the water dispenser has not been used for an hour or more, the wheel rotates through a greater arc to expose the active channel to one or more UV-C emitters, and for an extended time. The particular timing and degree of rotation may be set by the producer or user, based upon experience with microbial growth on the water dispenser or at a particular location.

A timer may be provided for actuating and terminating ultraviolet emissions from the emitters. Ultraviolet emission may be actuated for a preset time, such as 30 seconds. Ultraviolet emission may be coordinated with movement of the wheel. For example, after termination of water flow from the active channel, the wheel rotates to another position, and the active channel is now within the housing, and is in position to receive radiation from at least one of the emitters. UV-C emission is actuated for a period of time, and is then terminated. If the radiation emission period is brief, the likelihood of human exposure to ultraviolet radiation is reduced, while still being effective to kill pathogens. Alternatively, a timer may actuate radiation emissions for a period of time (which may be selectable), and terminate radiation emissions for a period of time, with radiation emission occurring independently from dispensing of water from the device.

A separate drain 42 may be provided for the wheel 38 and housing 10 that collects and disposes of water that inadvertently flows from the wheel. The separate drain may communicate with the drain 44, which communicates with the runoff surface 12.

The UV-C emitters may be UV-C emitting bulbs. The UV-C emitters may be UV-C emitting light emitting diodes.

The invention may be incorporated into the design of new drinking fountains, or it may be retrofitted to existing fountains.

What is claimed:

1. A liquid dispenser, comprising:
a rotatable member comprising a liquid inlet and a plurality of liquid outlets that communicate with the liquid inlet;
an emitter that emits ultraviolet radiation toward surface of the rotatable member comprising the liquid outlets;
a motor that drives the rotatable member;
an actuator that actuates the motor to drive the rotatable member;
wherein, in use, liquid is dispensed for a period of time from one of the plurality of outlets of the rotatable member, and the motor drives said one of the plurality of outlets of the rotatable member to a position to receive ultraviolet radiation from the ultraviolet emitter.

2. A liquid dispenser as described in claim 1, further comprising a spout, wherein said one of the plurality of outlets aligns with an opening in the spout and upon cessation of dispensing of liquid from said one of the plurality of outlets, said one of the plurality of outlets rotates to a position that is not aligned with the opening in the spout.

3. A liquid dispenser as described in claim 1, further comprising a spout, wherein the spout comprises a recessed portion having an opening therein, and wherein said one of the plurality of outlets aligns with the opening in the recessed portion of the spout and upon cessation of dispensing of liquid from said one of the plurality of outlets, said one of the plurality of outlets rotates to a position that is not aligned with the opening in the spout.

4. A liquid dispenser as described in claim 1, further comprising a spout, wherein the spout comprises a dish shaped recessed portion having an opening therein, and wherein said one of the plurality of outlets aligns with the opening in the recessed portion of the spout and upon cessation of dispensing of liquid from said one of the plurality of outlets, said one of the plurality of outlets rotates to a position that is not aligned with the opening in the spout.

5. A liquid dispenser as described in claim 1, further comprising a spout, wherein the spout comprises a dish shaped recessed portion having an opening therein, and wherein said one of the plurality of outlets extends above the opening in the recessed portion of the spout and upon cessation of dispensing of liquid from said one of the plurality of outlets, said one of the plurality of outlets rotates to a position that is not aligned with the opening in the spout.

6. A liquid dispenser as described in claim 1, wherein, in use, after liquid is dispensed for a period of time from said one of the plurality of outlets of the rotatable member, the motor drives another of the outlets in position for dispensing water after said another of the outlets has received radiation emitted from the radiation emitter.

7. A liquid dispenser as described in claim 1, wherein the rotatable member is formed as a wheel, and wherein the outlets are substantially equally spaced about a circumference of the rotatable member.

8. A liquid dispenser as described in claim 1, further comprising a switch that actuates dispensing of liquid from said one of the plurality of outlets, upon termination of dispensing of the liquid the rotatable wheel rotates.

9. A liquid dispenser as described in claim 1, further comprising a spout, wherein said one of the plurality of outlets aligns with an opening in the spout and upon cessation of dispensing of liquid from said one of the plurality of outlets, said one of the plurality of outlets rotates to a position that is not aligned with the opening in the spout, and further comprising a switch that actuates dispensing of liquid from said one of the plurality of outlets, upon termination of dispensing of the liquid the rotatable wheel rotates.

10. A liquid dispenser as described in claim 1, wherein the liquid dispenser is a water fountain.

11. A liquid dispenser as described in claim 1, wherein the rotatable member comprises at least three outlets.

12. A liquid dispenser as described in claim 1, wherein the rotatable member and the radiation emitter are contained within a decontamination unit.

13. A liquid dispenser as described in claim 1, comprising a plurality of radiation emitters.

14. A liquid dispenser, comprising:
    a rotatable member comprising a liquid inlet and a plurality of liquid outlets that communicate with the liquid inlet;
    an ultraviolet emitter that emits ultraviolet radiation toward surface of the rotatable member comprising the liquid outlets;
    a motor that drives the rotatable member;
    an actuator that actuates the motor to drive the rotatable member;
    a spout that extends above a runoff surface;
    wherein, in use, liquid is dispensed for a period of time from one of the plurality of outlets of the rotatable member, and upon cessation of dispensing of liquid from said one of the plurality of outlets, the motor drives the rotatable member to a position for said one of the plurality of outlets to receive ultraviolet radiation from the ultraviolet emitter, and wherein said one of the plurality of outlets communicates with an opening in the spout to dispense liquid through the opening in the spout, wherein liquid dispensed by said one outlet of the plurality of outlets is collected by said runoff surface.

15. A liquid dispenser as described in claim 14, wherein said one of the plurality of outlets aligns with an opening in the spout and upon cessation of dispensing of liquid from said one of the plurality of outlets, said one of the plurality of outlets rotates to a position that is not aligned with the opening in the spout.

16. A liquid dispenser as described in claim 14, wherein the spout comprises a recessed portion having an opening therein, and wherein said one of the plurality of outlets aligns with the opening in the recessed portion of the spout and upon cessation of dispensing of liquid from said one of the plurality of outlets, said one of the plurality of outlets rotates to a position that is not aligned with the opening in the spout.

17. A liquid dispenser as described in claim 14, further comprising a spout, wherein the spout comprises a dish shaped recessed portion having an opening therein, and wherein said one of the plurality of outlets aligns with the opening in the recessed portion of the spout and upon cessation of dispensing of liquid from said one of the plurality of outlets, said one of the plurality of outlets rotates to a position that is not aligned with the opening in the spout.

18. A liquid dispenser as described in claim 14, further comprising a spout, wherein the spout comprises a dish shaped recessed portion having an opening therein, and wherein said one of the plurality of outlets extends above the opening in the recessed portion of the spout and upon cessation of dispensing of liquid from said one of the plurality of outlets, said one of the plurality of outlets rotates to a position that is not aligned with the opening in the spout.

19. A liquid dispenser as described in claim 14, wherein, in use, after liquid is dispensed for a period of time from said one of the plurality of outlets of the rotatable member, the motor drives another of the outlets in position for dispensing water after said another of the outlets has received radiation emitted from the radiation emitter.

\* \* \* \* \*